United States Patent [19]
McNamara et al.

[11] Patent Number: 5,147,370
[45] Date of Patent: Sep. 15, 1992

[54] NITINOL STENT FOR HOLLOW BODY CONDUITS

[76] Inventors: Thomas O. McNamara, 919 Levering #505, Los Angeles, Calif. 90024; Gregory Mednik, 1530 N. Pointettia Place #221, Los Angeles, Calif. 90046

[21] Appl. No.: 713,770

[22] Filed: Jun. 12, 1991

[51] Int. Cl.$^5$ .................... A61M 5/00; A61B 17/00
[52] U.S. Cl. .................... 606/108; 606/194; 623/1
[58] Field of Search .................... 604/96, 104, 281; 606/108, 194, 195, 198; 623/1

[56] References Cited

U.S. PATENT DOCUMENTS

| | | | |
|---|---|---|---|
| 3,868,956 | 3/1975 | Alfidi et al. | |
| 4,411,655 | 10/1983 | Schreck | |
| 4,425,908 | 1/1984 | Simon | |
| 4,494,531 | 1/1985 | Gianturco | |
| 4,503,569 | 3/1985 | Dotter | |
| 4,512,338 | 4/1985 | Balko et al. | |
| 4,665,906 | 5/1987 | Jervis | |
| 4,733,665 | 3/1988 | Palmaz | 604/104 |
| 4,762,128 | 8/1988 | Rosenbluth | 604/96 |
| 4,776,337 | 10/1988 | Palmaz | 604/194 |
| 4,795,458 | 1/1989 | Regan | 606/194 |
| 4,800,882 | 1/1989 | Gianturco | 606/194 |
| 4,878,906 | 11/1989 | Lindemann et al. | 623/1 |
| 4,913,141 | 4/1990 | Hillstead | |
| 5,019,085 | 5/1991 | Hillstead | |
| 5,037,427 | 8/1991 | Harada et al. | 623/1 |

OTHER PUBLICATIONS

Nitinol-Unique Wire Alloy With A Memory by W. J. Buehler, et al., *Wire Journal*, Jun. 1969, pp. 41–49.
A Vena-Cava Filter Using Termal Shape Memory Alloy by Simon, et al., *Radiology*, vol. 125 (Oct., 1977) pp. 89–94.
Shape Memory Alloys by L. McDonald Schetky, *Scientific American*, Nov., 1979, pp.76–82.
Transfermoral Placement of Intraluminal Polyurethane Prosthesis for Abdominal Aortic Aneurysm by Balko, et al. *J. of Surg. Res.*, vol. 40, Apr., 1986, pp. 305–309.
Transluminal Expandable Nitinol Coil Stent Grafting: Preliminary Report by Dotter, et al. *Radiology*, No. 147, Apr., 1983, pp. 259–260.
Non-Surgical Placement o Arterial Endoprosthesis: A New Technique Using Nitinol Wire by Cragg, et al. *Radiology*, No. 147, Apr., 1983, pp. 261–263.
Roentgenoendoesophageal Prosthesizing with Nitinol Spiral (Russian) *Surgery*, 1989, pp. 87–94.
Device to Keep Clogged Arteris Open Falls Short of Scientists' Expectations *Wall Street Journal*, Jan. 3, 1991, p. 134.

*Primary Examiner*—Stephen C. Pellegrino
*Assistant Examiner*—Glenn K. Dawson
*Attorney, Agent, or Firm*—Michael J. Ram

[57] ABSTRACT

Disclosed is a coil stent constructed from a nitinol alloy having the ends thereof shaped to interact with a placement device specifically designed to hold the stent in a reduced diameter while it is being maniuplated to its desired position in the patient's body. The placement device is a hollow tube which has holes in it surface allowing placement of the ends of the stent therethrough so that they can be held in place inside the interior of the placement device by a mandril which is threaded through the center of the placement device. The combination of the features of the shapes on the end of the stent, the holes in the placement device and the mandril which passes through the placement device and the shapes on the end of the stent allow the interventional radiologist to accurately and rapidly place the stent in its desired position before it changes shape to its final pre-set configuration.

10 Claims, 2 Drawing Sheets

NITINOL STENT FOR HOLLOW BODY CONDUITS

BACKGROUND

The reconstruction of obstructed vital body organs to restore their function is a common and significant surgical task. In order to accomplish this task, surgeons have to perform extensive, traumatic operations with considerable morbidity and significant risk of severe complications and death. Therefore, it is desirable that alternative procedures be developed which allow the achievement of the same purpose with less risk and minimal surgical intervention.

With the advent of interventional radiology, researchers have developed techniques which effect the clearing of obstructions in many body conduits with little, if any, surgical intervention. The present invention relates to an improved nitinol spiral stent for use as an endoprosthesis for reinforcing these body conduits so as to maintain their patency and function. The invention has been demonstrated to have particular utility for repairing narrowed, weakened, distorted, distended or otherwise deformed tubular body conduits, such as those in the vascular, biliary, genitourinary, gastrointestinal and respiratory systems. The invention includes an improved delivery system for placement of the stent.

Previous devices for performing this function have not been designed for easy, controlled placement. Because the prior art stents were not designed to cooperate with specific placement devices and the placement devices were not designed to restrain the stent until properly located, correct placement was difficult to control. Also, prior nitinol stent systems required injection of cold saline, hot saline or both to prevent, control or encourage the transformation of the stent to its pre-set coil shape. This complicated the procedure and subjected the patient's body to unnecessary stress caused by the injection of the hot and cold fluids.

It is known in the art to utilize stents to reinforce tubular body conduits. Dotter (*Investigative Radiology*, Sep.–Oct. 1969, pp. 329-332) reported on unsuccessful experimental implantation of impervious plastic tube grafts and silicone coated stainless steel springs. In the same paper he also reported the successful (2.25-2.5 year patency) placement of coil springs made from standard No. 5 stainless steel wire. These coil springs were transported to the body site by a mandril with the coil tightly wrapped on its outer surface.

Additionally, it is known to utilize shape memory materials to fabricate these stents. The shape-memory effect was presented by A. B. Greininger of Harvard and V. G. Mooradian of MIT as early as 1938. Since then, several investigators have shown that there are several different types of alloys which demonstrate this property. More recently, U.S. Pat. No. 4,950,258 describes a molded coil produced from shape-memory polymers of lactide homopolymers, glycolide homopolymers, or copolymers of lactide and glycolide. However, this phenomena was not widely known until 1962 when Buehler announced the development of shape-memory materials prepared from titanium-nickel (TiNi) alloys, usually referred to as nitinol. Shape-memory alloys have the unusual property of mechanical "memory." These materials can be formed into a first predetermined shape above a transition temperature range (TTR), the TTR being dependent on the particular ratio of metals in the alloy. Below the TTR the alloy is highly ductile and may be plastically deformed into a second desired shape. Upon reheating above the TTR the alloy returns to its first pre-set form.

The general properties of these TiNi shape-memory materials are related in an article by W. J. Buehler, et. al., *Wire Journal*, June, 1969, pp. 41-49, and more extensively discussed in an article by McDonald Schetky (*Scientific American*, November, 1979, pp. 74-82). Schetky reviews several promising medical applications of the TiNi alloys including mounting means for orthopaedic implants, bone fracture binding systems, and implantable blood clot filters which can be inserted in a blood vessel through a catheter. These blood clot filters are further detailed in U.S. Pat. No. 4,425,908 to Simon, U.S. Pat. 4,494,531 to Gianturco, and Simon, M., et. al., Radiology, October, 1977, pp. 89-94.

The Simon device uses a nitinol material with a TTR of 40-50° F. The alloy, which can be formed into various mesh or filter designs, is reformed into a straight wire in ice-cooled water. A stud attached to the rear of the straightened filter wire is engaged in a notch on the guide wire which is then placed in the bore of a Teflon catheter for implantation. Under fluoroscopic control the catheter is advanced to the desired placement location within the blood vessel, and the guide wire and free end of the nitinol wire are extruded from the catheter. As the straightened nitinol wire becomes exposed to the temperature of the blood, it reforms into its pre-set filter shape locking it into the blood vessel and, as the notch on the guide wire with inserted stud on the straightened wire are extruded from the placement catheter, the wire automatically becomes disengaged from the placement device.

Other medical applications of shape-memory alloys in medicine are a prosthetic pump (U.S. Pat. No. 3,827,426), an apparatus for percutaneous catheterization (U.S. Pat. No. 4,411,655), an intrauterine contraceptive device (U.S. Pat. No. 3,620,212), a ring to hold a sewing cuff to an artificial heart valve (U.S. Pat. No. 4,233,690), a catheter or cannula (U.S. Pat. No. 3,890,977), marrow nails (U.S. Pat. No. 4,170,990), and dental arch wires (U.S. Pat. No. 4,037,324). Also, U.S. Pat. No. 4,665,906 addresses the use of stress-induced martensite alloys for the formation of several different medical devices.

Most relevant to the present invention are the products described by Dotter ("Transluminal Expandable Nitinol Coil Stent Grafting: Preliminary Report," *Radiology*, 147, April, 1983, pp. 259-260 and U.S. Pat. No. 4,503,569), Cragg, et. al., ("Nonsurgical Placement of Arterial Endoprothesis: A New Technique Using Nitinol Wire," *Radiology*, 147, April, 1983, pp. 261-263), Alfidi, et. al., U.S. Pat. No. 3,868,956 and Balko (Transfemoral Placement of Intraluminal Polyurethane Prosthesis for Abdominal Aortic Aneurysm, *Journal of Surgical Research*, 40, April, 1986, pp. 305-309; and U.S. Pat. No. 4,512,338). The Dotter article discloses the use of a nitinol material having a transition temperature of 130°-140° F., thus, requiring an injection of hot saline to cause the material to reform to its coil shape. Despite the specific requirement for hot saline, the Dotter patent claims a nitinol material with a transition temperature in a range at or above normal body temperature. Because the Dotter patent does not incorporate any means to restrain the coil during insertion, the placement procedure requires an initial injection of cold saline to insure the coil does not reform during insertion followed by a second injection of hot saline to encourage reformation. Cragg utilizes a threaded adapter on one end of the coil to hold it during placement. Alfidi discloses an appliance expansible by the application of electrical heating. Balko discloses a nitinol wire with a transition temperature below body temperature. In order to prevent the stent from changing shape while being positioned in the body it is enclosed in an insulating sheath.

G. Mednik, in an article entitled "Roentgeno-endoesophageal Prosthesing with Nitinol Spiral," published in the Russian journal *Surgery*, pp. 87-94 (1989), along with other clinicians, reports on the use of nitinol stents to clear obstruction in the esophagus of cancer patients. The placement procedure described therein restrains only one end of the stent, leaving it free to deform as it is heated by the patient's body temperature.

All of the stents described in the prior art patents and articles suffer from the same deficiencies. The stents and delivery systems are not designed to work together to allow accurate and controlled placement of the device.. while the shape-memory property of the nitinol materials is utilized, maximum advantage of this property cannot be realized because the design of the prior art delivery systems does not adequately control the transformation of the stent from its cold temperature form to the pre-set form attained above its TTR. A potential problem of nitinol alloys with a high TTR (i.e., 130°-140° F.) is they could be easily deformed in situ at body temperature. Unrestrained nitinol stents having a TTR below body temperature require rapid placement as they will start transforming to their original shapes as soon as they are introduced into the body or blood stream.

Thus, there is a need for a stent and delivery system which overcomes these problems.

SUMMARY

The present invention is directed to a coil stent constructed from nitinol alloy, the stent having the ends thereof designed to interact with a placement device specifically fabricated to retain the stent in a second smaller diameter while the stent is manipulated to its desired position in the patient's body. Additionally, it is directed to a placement device designed to utilize the structure on the ends of the stent to restrain the stent from reformation until in its desired location.

DRAWINGS

These and other features, aspects and advantages of the present invention will become better understood with reference to the present description, appended claims and accompanying drawings, where:

DESCRIPTION

Roentgeno-endoprosthetic placement (REP) involves the implantation into vessels and organs of a radiopaque prosthesis of metal alloy having a shape memory effect. The placement procedure is performed non-surgically by an interventional radiologist using modern imaging techniques which obviate the need to surgically expose the area to be treated. The technique takes advantage of the shape memory behavior of nitinol. When cooled below its TTR, a spiral of nitinol wire can be straightened into a linear configuration or twisted into a desired shape to fit the profile of the placement device upon which the nitinol wire will be carried to the body site to be treated. When heated to a temperature above the alloy TTR, the wire re-acquires its initial shape forming a frame within the body conduit being treated.

The nitinol prosthesis of the invention has the following characteristics:

1. Biological compatibility.
2. Resistance to corrosion.
3. Capability of placement using a catheter.
4. Accurate adjustment under radiological control.
5. Restoration of shape at a temperature lower than body temperature.
6. Fixation in situ.
7. Maintenance of the shape of vascular biliary, gastrointestinal, genitourinary, respiratory conduits (incompressibility under outside pressure).
8. Non-absorption of undesirable biological materials to the prosthesis surface, i.e., salts of bile acids, etc.

Figure 1:
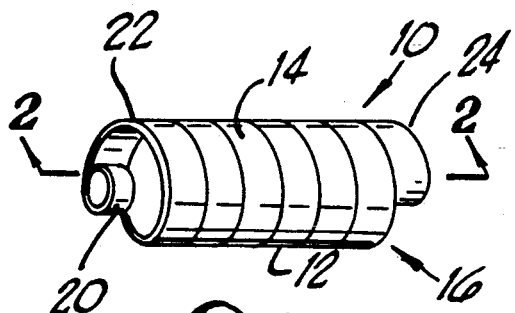
FIG. 1 is a side view of the coil stent in its first or expanded form according to the present invention.

With reference to the drawings, the stent 10 is composed of a coil 12 constructed from a nickel/titanium metal alloy (nitinol) wire 14 preferably of 55% nickel and 45% titanium. The wire 14 which is formed at a temperature above the TTR of the alloy into its first shape or configuration 16 can be reformed into a second configuration 18 when cooled below the TTR of the alloy. The wire 14 can be returned to its first configuration 16 by exposure to a specified higher temperature above the alloy TTR. FIG. 1 shows the stent 10 comprising a spiral of nitinol wire 14 in its first coiled configuration 16. Loops or hooks 20 as shown in FIGS. 1, 5, 6 and 8 are formed in the proximal and distal ends 22 and 24 to hold the wire 14 in place after placement on the delivery catheter 30.

In prior art devices, because the coil 12 was not restrained, the configuration could change during introduction of the coil into the body as the device warmed in response to body temperature. An uncontrolled change in configuration could result in damage to the vessel or other body conduit. Because the implant was not restrained, there was also a possibility that the endoprosthesis would not be precisely placed. Lack of precision could cause harm and/or lead to an unintended result. Thus, a metal alloy having a TTR close to normal body temperature was desired to delay or minimize a shape change while the stent was being implanted.

The endoprosthesis can also incorporate a silicone or other suitable biocompatible coating. This coating reduces the chance of thrombosis in treated blood vessels or adherence of food, bile, and genito-urinary deposits on the coil which would impair the function of the vessels or tubular structure when implanted therein. If undesired depositions occur, a partial or complete blockage of the treated vessel or tubular system can result, leading to jeopardy to life and limb. The coating must be chosen for the body system into which the stent will be placed. For example, coatings suitable for placement in arterial or venous blood vessels may not be suitable for genito-urethral tracts or the respiratory system. Appropriate coatings include, but are not limited to, silicone rubbers, hydrophilic polymers, biological coatings, such as heparin or other polysaccharides, collagen and other related materials which are known to retard deposition of undesirable materials, encourage desired tissue ingrowth or stimulate the deposition of preferential biological constituents.

Figure 2:
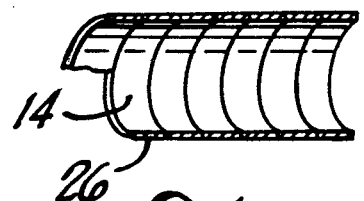
FIG. 2 is a vertical cross-sectional perspective view of the stent of FIG. 1 taken along line 2—2 of FIG. 1.

While products are usually composed of wire with a circular cross-section, further improvement, shown in FIG. 2, comprises utilization of a rectangular cross-section 26 for the wire which makes up the coil. This results in a tighter junction between adjacent loops in the coil which decreases or prevents ingrowth of invasive cancer tissue through the implanted device or deposition of undesirable blood components on underlying tissue damaged by angioplasty or other procedures used to clear clogged blood vessels.

Figure 5:
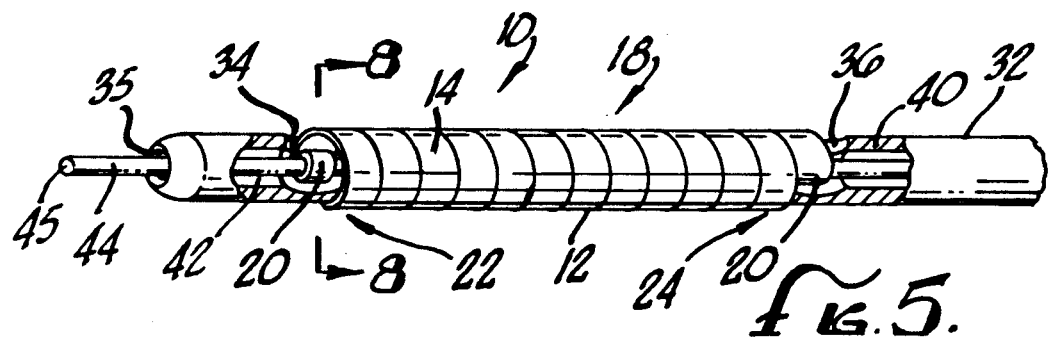
FIG. 5 is a partial cut away view of the stent of FIG. 1 in its second or delivery shape positioned in the delivery catheter of FIG. 3.

Also presented is a new and novel delivery system 30 for inserting the coil 12 which uses retention means such as fixing loops or hooks 20 at each end of the coil 10. This delivery system 30 includes a tubular placement device, such as a catheter 32, which has proximal and distal cut-outs or holes 34 and 36 in its outer surface 38, allowing the loops or hooks 20 to be inserted through the wall 40 of the catheter 32 and into the bore or lumen 42 of the catheter 32 where they can be traversed or pierced by a central mandril or guide wire 44 placed within the bore of the catheter 32 as shown in FIG. 5. The preferred design utilizes a catheter with an opening 35 in its proximal end so that the guide wire 44 can extend out of the catheter and through a constriction which will receive the stent. Placement of the mandril 44 through the loops 20 on the proximal and distal ends 22 and 24 of the coil 12 holds the wire 14 in its second configuration 18 so that it cannot reform to its first configuration 16 or be dislodged until the mandril 44 is withdrawn, thus ensuring proper positioning of the stent 10 in its desired final location. While not necessary, within the bore 42 of the catheter 32 at approximately the location of the proximal and distal cut-outs 34 and 36 are circular grooves 48 which allow additional space within the catheter 32 for the loops 20 as shown in cross-sectional view of FIG. 8. Holding the wire 14 in its second configuration 18 (cold temperature shape) until located in the desired position and then releasing the proximal end 22 of the wire by slightly withdrawing the mandril 44 from its position within the loop 20 on the proximal end 22 allows the wire 14 to reform into its first configuration 16 at the exact desired location in the body, greatly enhancing the effectiveness and safety of the stent 10 and the placement procedure.

Figure 3:
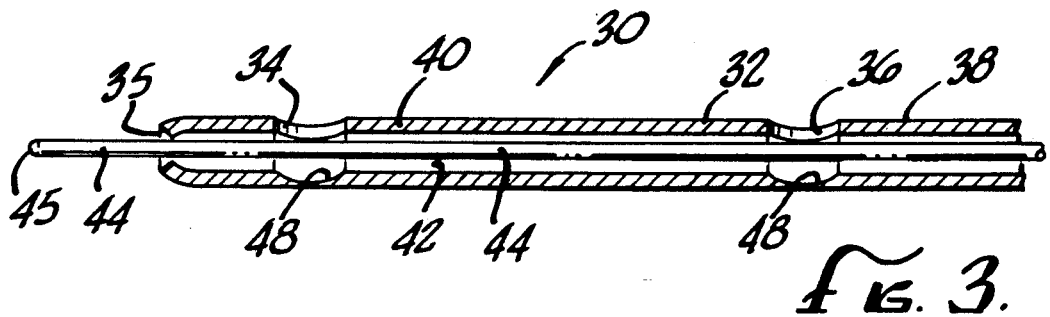
FIG. 3 is a cut away view of the delivery catheter and wire guide according to the present invention.
Figure 4:
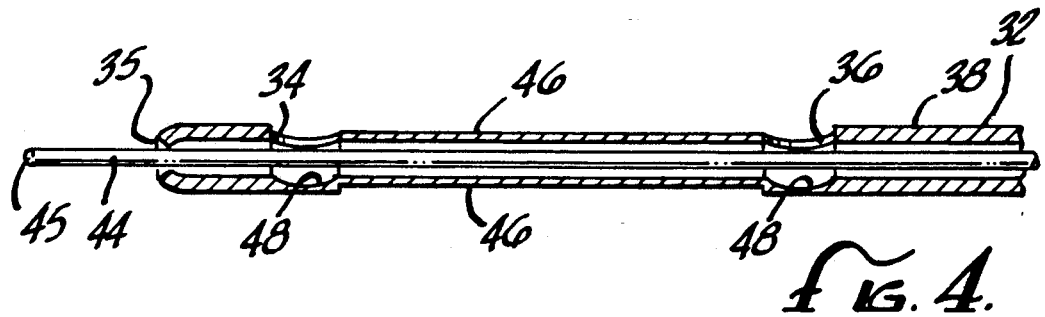
FIG. 4 is a cut away view of a variation of the catheter of FIG. 3.
Figure 6:
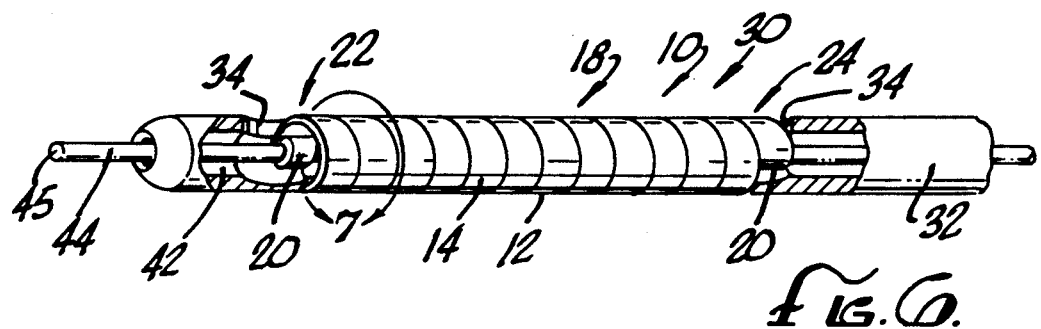
FIG. 6 is a partial cut away view of the stent of FIG. 1 in its second or delivery shape positioned in the delivery catheter of FIG. 4.
Figure 7:
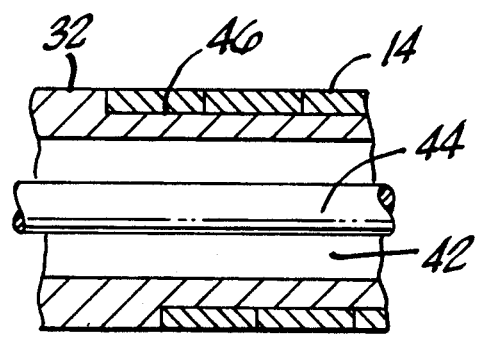
FIG. 7 is an enlarged view of a portion of the catheter and stent of FIG. 6.
Figure 8:
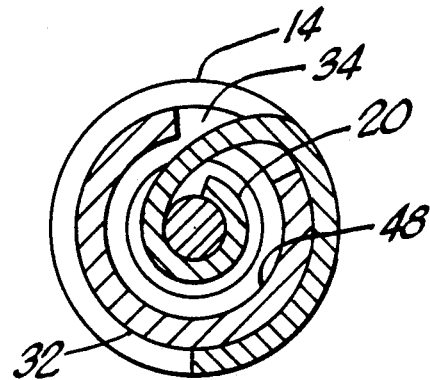
FIG. 8 is an enlarged cross-sectional view taken along line 8—8 of FIG. 5.

FIGS. 4 and 6 show a modification of the delivery system 30 which incorporates a depressed region 46 in and fully encircling the outer surface 38 of the catheter 32. The purpose of the depressed region 46 is to allow the wire 14 to be wrapped around the catheter 32 while still retaining the uniform outer profile of the catheter 32. ..As can be seen in FIG. 5, when the wire 14 is wound on the catheter 32 of FIG. 3, the wire increases the diameter of the system depressed region 46 shown in FIGS. 6 and 7, allows the wire 14 to be wrapped on the catheter 32 without increasing the outer diameter of the system, thus, making it easier to insert the system into the desired body organ.

The procedure for placing the stent 10, using the delivery system 30 of the present invention, within a blood vessel, for example, an artery following an angioplasty procedure, is as follows:

1. A wire 14 formed from a nitinol alloy with a TTR at or below body temperature is heated above its TTR to a temperature necessary to form a first configuration, i.e., a coil as shown in FIG. 1. A suitable form is a closely spaced coil, preferably with the coil turns touching each other, having an outer diameter slightly greater than the inner diameter of the vessel into which it will be placed. A loop or hook 20 is formed on each end of the wire. This can be accomplished in the hospital facility if suitable heating and forming equipment is available. Alternatively, the stent is supplied by the manufacturer in a range of pre-set outer diameters so that the interventional radiologist can select the dimensions most suited to the patient's needs.

2. The formed coil is then cooled below the TTR of the alloy so that it can be reshaped into a desired second configuration.

3. The loop 20 on the distal end 24 is placed through the distal cut-out 36 of the catheter 32 into the circular groove 48 and the mandril tip 45 is threaded through loop 14.

4. The wire is spirally wound tightly around the outer surface 38 of the depressed region 46 of the catheter 32, the loop 20 on the proximal end 22 of the wire 14 is inserted through proximal cut-out 34, and the mandril tip 45 is advanced through the loop 20 into the proximal end of the catheter 32.

5. The delivery system 30 with the wire 14 in its second configuration 18 is then introduced into the body, using readily available catheter introduction system, and advanced to the site for stent 10 placement under fluoroscopic or other nonsurgical visualization procedures.

6. When the distal end 24 of the wire 14 is located at the distal end of the chosen delivery site the mandril 44 is partially withdrawn, freeing the proximal end 22 of the wire 14.

7. Having been exposed to body temperature, which is above the TTR of the alloy, the wire 14 will immediately reform into its first configuration 16 (a coil of outer diameter greater than the vessel in which it is placed).

Figure 9:
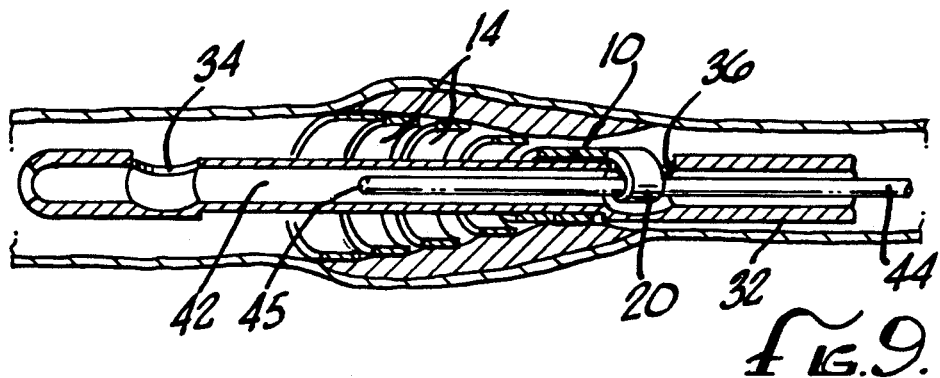
FIG. 9 is a partial sectional view of an artery following angioplasty showing the delivery system of FIG. 4 with the stent in the process of reforming to its high temperature configuration.

8. Once the proximal end is sufficiently reformed to hold the stent 10 in the vessel, as shown in FIG. 9, the mandril 44 can be withdrawn from the loop 20 on the distal end 24 of the wire 14. If the stent 10 is not properly positioned, it can be moved and repositioned before the mandril 44 is withdrawn from the distal loop.

Alternatively, the hook and loop 20 can be formed on the ends of the wire while it is in its second low temperature configuration.

In a like manner, the stent can be positioned in various tubular or hollow body conduits or organs.

The delivery system 30 for the improved nitinol stents 10 takes advantage of the fixing loops 20 at both ends of the coil 12. Specifically, this delivery system 30 comprises both a catheter 32 and guide wire 14, with the overall system having a significantly smaller diameter than the prior art delivery systems. The catheter 32 of the improved delivery system 30 has at least two cut-outs 34 and 36 in its outer surface 38 enabling the loops (or hooks) 20 to be placed through the wall 40 of the catheter 32 and then traversed by a central guide wire 44 placed within the catheter 32. The placement of the central guide wire 44 through the catheter lumen 42 and the loops or hooks 20 placed therein affixes the coil 12 so that it cannot reform or be dislodged until the guide wire 14 is withdrawn. This ensures proper positioning prior to release of the endoprosthesis (stent 10), allows the stent to be withdrawn or repositioned if problems occur during the procedure, thus, greatly enhancing the effectiveness and safety of the procedure.

Additional beneficial features of the delivery system are reduction of friction and an increase in flexibility and steerability. The coating on the product, while reducing deposits on the system, also reduces friction as the system is manipulated to its desired location. The smaller diameter of the catheter and the commensurate flexibility, in combination with standard catheter steering techniques, allows the interventional radiologist to readily manipulate the catheter through stenotic (narrow) passages and to bend the catheter to direct the endoprosthesis to its desired location, thus, allowing access to regions that are difficult to access due to the tortuous course between the sites of introduction and implantation.

As a further improvement, an angioplasty balloon can be combined with the nitinol endoprosthesis. Specifically, this improvement incorporates an angioplasty balloon on a catheter having two or more inner channels. One channel is for inflating the angioplasty balloon and a second channel is for insertion of the wire guide to catch the terminal loops of the nitinol stent. Contrast media or other liquids can be injected through a third channel or through the channel used for the wire guide.

The combined system allows the interventional radiologist to perform balloon dilatation of a hollow body conduit and place the nitinol stent in a single, controlled nonsurgical procedure with one instrument through a single access site. This ensures greatly enhanced effectiveness and safety of the balloon dilatation procedure and proper positioning prior to the release of the stent, all in rapid succession.

EXAMPLE 1

Transcutaneous implantation of an endobiliary prosthesis in patients was performed as follows:

1. A metal guide was introduced beyond the stricture area using a previously placed external drainage catheter.
2. Using the Seldinger procedure, the external drainage tube was replaced by a transport catheter, the tip of which was placed immediately proximal of the stricture.
3. A coiled nitinol endobiliary prosthesis, fixed on the placement system described above, was introduced through the lumen of the transport catheter so that the end fixed in the proximal cut-out is located at the proximal stricture end.
4. The transport catheter was then removed so that the prosthesis, still mounted on the delivery catheter remained in the lumen of bile duct and across the stricture.
5. The forward loop was then released by slightly withdrawing the guide wire. Under body temperature, the prosthesis reformed to its pre-set spiral shape with a predetermined diameter slightly larger than the biliary tract.
6. Once the prosthesis was accurately fixed in the stricture, the second loop was released and the guide wire was removed.
7. The transport catheter was then replaced by an external drainage device which was removed seven days after the procedure.

EXAMPLE 2

Twenty-six experimental (animal) and 17 clinical endobiliary replacements were conducted using nitinol stents incorporating the invention described above and the procedure of Example 1. The procedure, as applied to one of the patients in this clinical study was as follows:

A 37-year old male was admitted to the hospital with symptoms of jaundice, weakness, pruritus and nausea. He had a history of several years of similar symptoms and had previously undergone stomach resection for cancer. Hospital admission diagnosis was cirrhosis of the liver. Scintigraphy revealed an enlarged liver with pronounced irregularity of colloid distribution. Ultrasound examination showed the liver to be enlarged due to changes in the left lobe. The walls of the intrahepatic biliary ducts were consolidated and the gallbladder was curved. The pancreas had even contours and its head was diffusely consolidated. Transcutaneous transhepatic cholangiography revealed dilatation of the intra and extra hepatic bile ducts and common bile duct obstruction due to tumor constriction. The patient was transferred to radiology with the diagnosis of an obstruction of common bile duct caused by the metastases from the stomach tumor. Under local anaesthesia, transcutaneous transhepatic dilatation of the stricture was performed with roentgeno-endobiliary prosthetic placement at the distal end of the obstruction. Prosthetic placement was not performed along the whole length of the stricture because the length of the prosthesis available at the time was insufficient. Therefore, six months later the patient underwent a repeated roentgeno-endobiliary prosthetic placement with a longer prosthesis sized to fit the full length of the stricture.

The control cholangiogram showed that the biliary ducts were patent. External drainage was removed on the third day. The cessation of jaundice and decrease in bilirubin level were observed.

| | Clinical Results | | |
|---|---|---|---|
| | Before Procedure | After Procedure | Normal |
| Total bilirubin | 176.7 m mol/L | 1.0 | (0.6–0.8) |
| Direct bilirubin | 194.4 m mol/L | 1.4 | (0.6–0.8) |
| Indirect bilirubin | 82.3 m mol/L | 0.4 | (0.6–0.8) |

One year after the procedure the patient continues to exhibit improvement over his pre-procedure condition.

The results clearly indicate that the procedure was effective and had continuing beneficial results.

EXAMPLE 3

During animal investigations 2 techniques of esophageal placement of stents (REP) were developed.

A. In the first technique, the spiral was formed with a fixing ring on its distal end. Then it was cooled using chloroethane ($C_2H_5Cl$), straightened, placed on a rod and inserted into the placement catheter. The catheter was inserted into the body organ to be treated with the fixing ring on the straightened nitinol spiral placed in the area of the lower end of the stricture. The spiral, responding to body heat, began to acquire the previously given shape. After the spiral reformed from its low temperature shape, it was disconnected from the placement rod and the rod was removed from the organ.

B. In the second technique, rather than fully straightening the nitinol spiral after cooling with chloroethane, the stent was twisted on the catheter of the invention into a spiral of a smaller diameter conforming to the catheters outer surface. Following disconnection from the catheter, the spiral enlarged in its diameter as a result of being exposed to the body temperature of the animal and was fixed inside the body organ (tubular conduit) forming an internal support.

All the stages of the procedure were conducted under direct x-ray imaging control. After the spiral was re-formed in situ a control electroroentgenogram was performed and follow-up roentgenoscopy was performed at various intervals thereafter. Displacement of the nitinol spiral was observed in 3 of 5 rabbits with esophageal burn stricture and in 3 of 20 rabbits with an intact esophagus. No rabbits with surgically caused esophageal strictures showed a shifting of the implanted spiral. Displacement of the spiral was observed in 8 of 37 rats. Based on the animal experiments it was concluded that the spiral diameter should exceed the diameter of the esophageal stricture or the tubular body organ receiving the implant by 2-3 mm and the diameter of the intact esophagus of rabbits by 3-4 mm to avoid displacement. The spiral diameter for the intact esophagus of rats should exceed the esophageal diameter by a ratio of 1.5.

Two months following the procedure, the inflammatory infiltration around spiral coils was considerably reduced. Granulations were replaced by fibrous tissue and, by the third month following the procedure, the spaces between the windings of the coil were formed of fibrous tissue with widely scattered single lymphoid cells being encountered. The channels located in the superficial layers of the mucous membrane were covered with multilayer flat epithelium.

Depending on the depth of impression of the spiral coils, the walls of the coil were covered either with multilayer flat epithelium (in the mucous membrane) or with fibrous tissue (in the submucous membrane).

EXAMPLE 4

Based on the results of the animal experimentation set forth in Example 3A and 3B human clinical REP were performed in 6 patients with esophagus cancer. All 6 were male patients, ages from 44 to 76 years and a mean age of 62. All patients had cancer of the thoracic section of the esophagus extending 50 to 80 mm. Many of the conditions were complicated by advanced age, severe pathology (as a rule cardiovascular), and metastatic cancer making it impossible to perform radical surgical procedures. The patients also responded negatively to gastrostomy. Taking into account the increasing dysphagia, a nitinol spiral endoprosthesis with lengths ranging from 45 to 80 mm, and diameters from 12 to 20 mm were implanted in each patient. Set forth below is a representative example:

Patient 1, 62-years old, complained of difficulty in passing solid and fluid food along the esophagus, weakness, hoarseness, cough, and pain in the thorax with radiation into the interscapular area. Medical consultation was sought three months after the patient noted the onset of the pains in the thorax. X-ray examination showed a 75 mm tumor of the bronchial segment of the esophagus with an ulceration of $25 \times 10 \times 10$ mm. Esophagoscopy showed round, whitish, easily bleeding formations ranging in size from 22 to 29 cm. There also was a dramatic circumferential stenosis of the esophageal lumen. Bronchoscopy showed compression of the left main bronchus with the lumen reduced to one-half its normal size. The diagnosis was Squamous cell cancer of the middle third of the esophagus with bronchial segment lesion, T3NxMo with exophytic type of growth with ulceration, chronic cerebrovascular insufficiency, and arteriosclerosis obliterans of the lower extremities vessels.

Taking into account the patient's age, concomitant pathology, radiologic and bronchologic signs, the impossibility of re-secting the tumor, and increasing dysphagia, it was decided to perform REP of the cancerous esophageal stricture with a spiral nitinol prosthesis of the present invention and to apply chemotherapy. Premedication was relanium 2.5 ml, atropinium 1.0 ml. Under x-ray control, balloon dilatation of the stricture was performed followed by the above-described catheter introducer with a twisted nitinol spiral mounted on its outer surface. The preformed endoprosthetic replacement consisted of a spiral with a 60 mm length and a 20 mm diameter. After being cooled with chloroethane the spiral was twisted around the placement catheter into a smaller diameter of 7.0 mm and it was then introduced into the esophagus. Guided by x-ray contrast marks fixed to the patient's skin, the introduction catheter with the spiral attached was introduced into the stricture with the distal end of the spiral located at the end of the stricture closest to the point of introduction of the placement catheter. The mandril wire was then withdrawn slightly releasing the proximal end of the spiral. The proximal end of the coil began acquiring the preformed shape under the influence of body temperature. To accelerate the process, 50 ml of water at 40°-50° C., was introduced into the esophagus along the catheter. After full expansion of the coil to its preformed shape the mandril wire was fully removed releasing the distal end of the implant, and the placement catheter and locking wire were extracted from the patient. Examination of the esophagus using contrast media showed the dilation of the lumen as expected. Subjectively, the patient felt no pain during the procedure. For the next few days the patient had the feeling of pressure on the esophageal walls in the thorax but it soon disappeared. The patient was then given chemotherapy with methotrexate and spirobromin. The patient reported the ability to ingest fluid and solid food through the esophagus; this was confirmed by clinical observations.

EXAMPLE 5

Using ethyl chloride to cool the nitinol it was reshaped for mounting on an 8F placement catheter which was then placed in an artery immediately after it had been expanded by angioplasty, such as the iliac, femoral, popliteal, subclavian, carotid or renal artery (more than 110 clinical implants). Experimental studies were conducted on 36 dogs with placement of 66 endovascular nitinol prostheses. Long term results followed up over a period of 14 months demonstrated acceptable prolonged performance of the nitinol stents. Morphological study showed that stents were separated in a ring-like fashion by a thin layer of connective tissue and the inner lumen of the coil was lined with a layer of epithelial cells.

The animal research and human clinical trials proved validity of the above-described invention and procedure, the ease of use, the accuracy and reliability of placement, and the biological compatibility of nitinol. The device and procedure is applicable to the placement of a support structure into any body conduit or tubular organ. It has been demonstrated to be effective for restoring a channel through esophageal tumors, improving flow through diseased blood vessels and bile ducts, the device also has utility in relieving obstructions in the intestinal or urogenital tract or other tubular body conduits or organs. Additionally, its utility is enhanced when combined with balloon dilation or laser recanalization of the obstructed conduit or organ being treated.

Because the system described herein has utility for supporting numerous body organs of various different sizes, the dimensions of the catheter, mandril and expandable shunt are varied to fit the organ in which they are being placed. Dimensions of the catheter and mandril are chosen to be comparable to other medical devices for fluid delivery or organ treatment currently used in these organs. The shunt dimensions depend on the size of the organ to be supported.

Testing has shown that the use of a nitinol spiral in combination with the delivery system of the invention for endoprosthetic placement is a minimally traumatic, relatively bloodless technique which can be applied without general anesthesia for improving the patency of body conduits and tubular organs.

What is claimed is:

1. A system for positioning in a hollow body organ an expendable stent having a first retention means formed on a first end of the stent and a second retention means formed on a second end of the stent comprising:

an elongated tube having a proximal end for placement into the hollow body organ, a distal end spaced from the proximal end, and a lumen extending through the tube from the proximal end to the distal end, said elongated tube having a first and second hole in the surface thereof, said first and second holes being separated from each other along the length of the tube and being located between the distal end and the promixal end of the tube, the holes extending from the exterior of the tube into the lumen and being sized so that the first retention means formed on the stent can be inserted through the first hole into the lumen and the second retention means formed on the stent can be inserted through the second hole into the lumen, a removable mandril extending through and enclosed within the lumen from at least the distal end to the proximal end of the tube, the mandril being sized to interlock with the first and second retention means on the stent which are positionable in the lumen of the tube.

2. The system of claim 1 wherein the outer diameter of the tube between the first and second hole is smaller than the outer diameter of the remainder of the tube.

3. The system of claim 1 wherein the lumen has a uniform diameter throughout the length of the catheter.

4. The system of claim 1 wherein the lumen has an enlarged diameter at the location of the first and second hole and a uniform but smaller diameter through the remainder of the length of the catheter.

5. A system for placing a support at a desired location in a tubular body organ comprising:

an elongated catheter having a proximal end for placement in the tubular body organ and a distal end spaced from the proximal end so that after placement of the proximal end in the tubular body organ at the desired location, the distal end extends out of the tubular body organ, at least one lumen extending through the catheter from the proximal end to the distal end, a first and second cut-out, each cut-out extending through the wall of the catheter into the lumen, the first cut-out being located near the proximal end of the catheter, the second cut-out being located distal to the first cut-out, an expandable stent comprising a wire of a fixed length having first and second attachment means formed on the ends of the wire, the wire being spirally wound around the outer surface of the catheter with the first attachment means being placed through the first cut-out and the second attachment means being placed through the second cut-out, an elongated removable mandril extending through the catheter lumen from the distal end at least past the first cut-out, the mandril retaining the first and second attachment means in the lumen in a releasable manner.

6. The system for placing a support of claim 5 wherein the wire is composed of a shape memory alloy which can be formed into a spiral conforming to the outer surface of the catheter at a first temperature and which reforms into a shape of dimensions different from the spiral by exposing the wire to a second temperature higher than the first temperature.

7. The system for placing a support of claim 6 wherein the shape memory alloy has a transition temperature range less than the normal temperature of the human body.

8. The system for placing a support of claim 7 wherein the alloy is nitinol.

9. A method of placing an internal support into a hollow structure utilizing a tubular placement device, the tubular placement device having a central lumen extending along its length comprising:

forming a fixed length wire of a shape memory alloy into a first shape sized to fit within and support the hollow structure, said wire having first and second retention means on the ends thereof, cooling the wire to a temperature below the transition temperature range of the shape memory alloy, placing the first retention means through a first opening in the wall of the tubular placement device, securing the first retention means within the lumen of the tubular placement device by advancing an end of a mandril along a portion of the length of the lumen and through the first retention means, wrapping the wire around the outer surface of the tubular placement device and placing the second retention means through a second opening in the wall of the tubular placement device into the lumen, securing the second retention means in the lumen by advancing the end of the mandril further along the length of the tubular placement device through the second retention means and past the second opening, advancing the tubular placement device with the wire wound on its outer surface into the hollow structure until the first retention means is at a desired location in the hollow structure, releasing the second retention means by withdrawing the end of the mandril to a point between the first and second opening in the wall, allowing the wire to at least partially reform to its first shape an amount sufficient to retain the wire within the hollow structure, said reformation being caused by exposing the wire to a temperature greater than the transition temperature range of the alloy, releasing the first retention means by withdrawing the end of the mandril past the first opening, and withdrawing the tubular placement device and mandril from the hollow structure.

10. The method of claim 9 wherein the hollow structure is a tubular organ in the human body and the tubular placement device is catheter sized to fit within the tubular organ.

* * * * *